United States Patent [19]

Barnicki et al.

[11] Patent Number: 6,011,163
[45] Date of Patent: Jan. 4, 2000

[54] USE OF FLUORINATED HYDROCARBONS AS REACTION MEDIA FOR SELECTIVE EPOXIDATION OF OLEFINS

[75] Inventors: Scott Donald Barnicki; John Robert Monnier, both of Kingsport, Tenn.

[73] Assignee: Eastman Chemical Company, Kingsport, Tenn.

[21] Appl. No.: 09/315,107

[22] Filed: May 20, 1999

[51] Int. Cl.⁷ .................................. C07D 301/10
[52] U.S. Cl. ........................... 549/534; 549/536
[58] Field of Search ...................... 549/534, 536

[56] References Cited

U.S. PATENT DOCUMENTS

| | | | |
|---|---|---|---|
| 2,814,628 | 11/1957 | Landau et al. | 260/348.5 |
| 3,458,535 | 7/1969 | Gozzo et al. | 260/348.5 |
| 4,994,588 | 2/1991 | Kapicak et al. | 549/534 |
| 5,362,890 | 11/1994 | Stavinoha, Jr. et al. | 549/536 |
| 5,618,954 | 4/1997 | Boeck et al. | 549/534 |

*Primary Examiner*—Ba K. Trinh
*Attorney, Agent, or Firm*—Matthew W. Smith; Harry J. Gwinnell

[57] ABSTRACT

The present invention is directed to a process for the selective epoxidation of non-allylic olefins. The process includes the step of contacting a gas mixture comprising a non-allylic olefin, oxygen, and a fluorinated hydrocarbon with a silver epoxidation catalyst at conditions effective to epoxidize the non-allylic olefin. The fluorinated hydrocarbon has a C—F bond dissociation energy of 110 kcal/mole or greater, and sufficiently non-acidic C—H bonds, if present, so as to avoid abstraction of HF from the fluorinated hydrocarbon under reaction conditions.

12 Claims, No Drawings

USE OF FLUORINATED HYDROCARBONS AS REACTION MEDIA FOR SELECTIVE EPOXIDATION OF OLEFINS

FIELD OF THE INVENTION

This invention pertains to an improved gas phase process for the selective epoxidation on non-allylic olefins wherein the process is carried out in the presence of certain fluorinated hydrocarbons. The fluorinated hydrocarbons useful in the present invention have C—F bond dissociation energies high enough such that C—F bond rupture does not occur at reaction temperature and have sufficiently non-acidic C—H bonds, if any, so as to avoid abstraction of HF from the fluorinated hydrocarbon.

BACKGROUND OF THE INVENTION

1. Flammability Limits

As explained in Lees, F. P., "Loss Prevention in the Process Industries, Volume 1," 485–86 (1980) and Coffee, R. D., Loss Prevention 13, 74–80, (1980), a flammable gas, e.g., methane, butane, ethylene, butadiene, and other hydrocarbons, burns in oxidizing environments only over a limited composition range. The limits of flammability (often called the explosive or hot flame limits) are the concentration extremes at which a mixture of a flammable gas and an oxidant can continue to burn once a flame is ignited by an external energy source such as a spark. These flammability extremes are a function of temperature, pressure, and composition. The explosive limit is usually expressed as volume or mole percent of flammable gas in a mixture of oxidant (usually oxygen), inert, and flammable gas. The smaller value is the lower (lean) limit and the larger value is the upper (rich) limit. For example, methane-oxygen mixtures will propagate flames for methane concentrations between 5.1 and 61 mole percent methane (i.e., 94.9 and 39 mole percent oxygen) and methane-air mixtures between 5.3 and 14 mole percent methane (i.e., 19.9 and 18 mole percent oxygen), at 25° C. and atmospheric pressure. In general, the lower explosive limit (LEL) decreases, and the upper explosive limit (UEL) increases as temperature and pressure increase, and amount of inert decreases. Below a certain oxygen content, called the minimum oxygen content (MOC), the mixture will not support combustion. For methane at 25° C. and 1 atmosphere, the MOC is 13.98 mole percent oxygen.

2. Diluents for Gas-Phase Epoxidation Reactions

When carrying out a highly exothermic reaction (e.g., epoxidation of butadiene or ethylene), it is important to design the reactor for adequate heat removal to prevent thermal runaway (uncontrollable reaction and generation of heat). A typical reactor configuration for operation of a highly exothermic reaction is a multi-tubular packed bed immersed in a flowing heat transfer fluid (often boiling water). In such a reactor, heat is removed via several mechanisms: (1) axial convection from the catalyst surface to the bulk gas feedstream; (2) radial convection through the catalyst and support particles to the tube walls and into the heat transfer fluid; and (3) radial conduction from the catalyst surface through the bulk gas to the tube walls and into the heat transfer fluid. If the tubes are too large in diameter (radial temperature gradient is large), the reactant or diluent gas has low heat capacity, or the gas flow is too low, hot spots will develop which can lead to a runaway reaction or catalyst deactivation.

Processes for the selective epoxidation of olefins which contain no allylic hydrogen atoms (non-allylic olefins) or olefins which contain hindered allylic hydrogen atoms are described by Monnier and Muehlbauer in U.S. Pat. Nos. 4,897,498; 4,950,773; 5,081,096; 5,138,077; and 5,145,968. Stavinoha and Tolleson disclose in U.S. Pat. No. 5,117,012 the selective epoxidation of 1,3-butadiene to 3,4-epoxy-1-butene (EpB) by contacting a mixture comprising 1,3-butadiene, oxygen, and methane with a supported silver catalyst at elevated temperatures. Stavinoha et al. disclose in U.S. Pat. No. 5,362,890 an improved process for the selective epoxidation of 1,3-butadiene to EpB wherein the ballast gas for the reaction is n-butane. Boeck et al. disclose in U.S. Pat. No. 5,618,954 a similar process for the epoxidation of 1,3-butadiene to EpB with nitrogen or $C_1$–$C_4$ hydrocarbons as the diluent.

The use of diluent gases in non-allylic olefin epoxidation, specifically the epoxidation of 1,3-butadiene to 3,4-epoxy-1-butene, is described in U.S. Pat. Nos. 5,362,890, and 5,618,954. U.S. Pat. No. 5,618,954 discloses that nitrogen and $C_1$–$C_4$ paraffinic hydrocarbons, especially methane, or mixtures thereof are the preferred diluents for the epoxidation of 1,3-butadiene to EpB. The oxygen:butadiene ratio in the reactor feed gas can be increased by using methane as the diluent over that with nitrogen as the diluent without the methane:oxygen:butadiene mixture becoming flammable.

U.S. Pat. No. 5,362,890 discloses the use of $C_2$–$C_6$ paraffin hydrocarbons as diluents for non-allylic olefin epoxidation. The data disclosed in this patent shows the advantages of using higher alkane hydrocarbons over methane, nitrogen, and other common diluents. The advantages cited include higher safe oxygen levels, higher epoxide production levels for the same reactor temperatures, and more stable operation due to better heat removal.

The use of diluent or ballast gases in ethylene epoxidation is described in Canadian Patent Nos. 1,286,687 and 2,053,404; and U.S. Pat. Nos. 3,119,837 and 5,057,481. According to these patents, the typical volumetric composition of feed gases used in such ethylene epoxidation processes comprise 5 to 50 volume percent ethylene, 2 to 8 volume percent oxygen, up to 7 volume percent carbon dioxide, up to 5 mole percent ethane with the balance being composed of an additional inert diluent such as nitrogen or methane.

U.S. Pat. No. 3,119, 837 discloses that selectivity of ethylene conversion to ethylene oxide can be enhanced by the addition of methane as a diluent. Methane serves as a heat sink, moderating temperature differentials within the reactor, and allows for more isothermal reactor operation. This patent further states that the benefits to selectivity and ease of operation do not extend to other paraffins normally encountered in commercially available ethylene, e.g., ethane and propane, due to excessive stripping of chlorine from the surface of the catalyst, which renders the catalyst unstable and, thus, susceptible to thermal runaway. Use of methane is also said to allow an increase in the oxygen:ethylene ratio in the reactor feed gas over the ratio with nitrogen, which increases conversion of ethylene to ethylene oxide.

According to Canadian Patent 1,286,687, other diluents that function as heat sinks include nitrogen, helium, argon, carbon dioxide, and lower paraffins such as methane and ethane. However, U.S. Pat. No. 5,057,481 discloses that the use of ethane at concentrations greater than about 5 mole percent results in reduced selectivity in the epoxidation of ethylene to ethylene oxide and lower thermal stability because the chloride concentration on the catalyst surface is lowered. Typical silver catalysts employed in the epoxidation of ethylene contain about 1 to 300 parts by million by weight (ppmw) of Cl on the catalyst surface, both to increase selectivity to ethylene oxide by lowering combustion of ethylene and ethylene oxide to carbon dioxide and water as well as to increase the thermal stability of the silver catalyst. If the level of Cl on the surface of the silver catalyst becomes too low, the reaction becomes excessively exothermic with accompanying loss of selectivity. Ethane acts as a chloride stripping agent and at concentrations above 5 mole percent and at temperatures typically employed in the epoxidation of ethylene, e.g., 230 to 280° C., the degree of chloride stripping becomes unacceptably excessive. As is disclosed in the above-cited patents, one of the problems associated with the use of carbon dioxide as a heat transfer agent (heat sink) in ethylene epoxidation processes is that at levels greater than about 7 mole percent carbon dioxide becomes a reaction inhibitor for ethylene oxide formation. Thus, the concentration of carbon dioxide in feed gas in ethylene epoxidation processes must be limited to concentrations of less than about 7 mole percent. At such low levels, carbon dioxide does not have an appreciable effect on the heat capacity nor the flammability characteristics of the reaction gas mixture.

Although much of the art discussed above has resulted in improvements in the efficiency, activity, and/or stability of the epoxidation catalyst, there still exists a need in the art to further improve and increase the efficiency, activity, and stability of such catalysts. Accordingly, one of the objects of the present invention is to provide a process that meets this need in the art.

SUMMARY OF THE INVENTION

Briefly, the present invention is directed to a process for the selective epoxidation of non-allylic olefins. The process includes the step of contacting a gas mixture comprising a non-allylic olefin, oxygen, and a fluorinated hydrocarbon with a silver epoxidation catalyst at conditions effective to epoxidize the non-allylic olefin. The fluorinated hydrocarbon has a C—F bond dissociation energy of 110 kcal/mole or greater, and sufficiently non-acidic C—H bonds, if present, so as to avoid abstraction of HF from the fluorinated hydrocarbon under reaction conditions.

DETAILED DESCRIPTION OF THE INVENTION

We have surprisingly discovered that certain fluorinated hydrocarbons can be used as major components of gas streams for the selective epoxidation of olefins. These fluorinated hydrocarbons are used at concentrations that would typically result in rapid and irreversible deactivation of Ag-based catalysts through the formation of AgF, the thermodynamically stable end product. The main benefit of this discovery is that feed compositions, e.g., the $O_2$ and $C_4H_6$ concentrations for butadiene epoxidation and the $O_2$ and $C_2H_4$ concentrations for ethylene epoxidation, can be increased such that the yield of the desired epoxide product is substantially increased, resulting in greater economic benefit. This, of course, requires that the active and selective Ag catalysts are stable in the presence of such high concentrations of fluorinated hydrocarbons. These fluorinated hydrocarbons are often used as flame retardant and flame extinguishants, and have physical and chemical stability that make them especially appropriate as inert diluents for feed streams that contact promoted Ag catalysts typically used for olefin epoxidation reactions.

It is noted that chlorinated hydrocarbons have also been used as flame retardant and flame extinguishants. However, the thermal and chemical instabilities of the chlorinated hydrocarbon compounds make them unsuitable for the purposes of this invention because total and irreversible loss of catalytic activity due to AgCl occurs when high concentrations of chlorinated hydrocarbons are exposed to promoted Ag-based catalysts.

Concentrations of inert, stable, fluorinated compounds in olefin and $O_2$ feedstreams in accordance with the present invention are much higher than the concentrations of organic chlorides typically added to feedstreams of olefin epoxidation gas feedstreams. Parts per million (ppm) levels of organic halides, typically chlorides (see Monnier et al., U.S. Pat. No. 4,950,773 (1990) and D. J. Hucknall, "Selective Oxidation of Hydrocarbons", Academic Press, London, 1974, pp. 6–19) are continually added to the feedstream to maintain selectivity and thermal stability during olefin epoxidation. Organic fluorides have also been added in ppm levels to the feedstreams of olefin epoxidation reactions to maintain selectivity and thermal stability. Kapicek et al. in U.S. Pat. No. 4,994,588 (1991) describe the addition of the class of fluorinated hydrocarbons known as "Freons" to the olefin and $O_2$ containing feedstream. The concentration of fluorinated hydrocarbons is maintained between 0.1 and about 2,000 ppm, by volume, of the overall feedstream. For the successful use of fluorinated hydrocarbons in U.S. Pat. No. 4,994,588, it is also required that the fluorinated hydrocarbons undergo partial decomposition during reaction. Thus, the use of fluorinated hydrocarbons in U.S. Patent No. 4,994,588 falls outside the scope of the present invention.

Our discovery requires the addition of substantially higher concentrations of fluorinated hydrocarbons that are stable under reaction conditions normally used for olefin epoxidation. The concentrations of the fluorinated hydrocarbon used in our invention are typically between about 5 and about 70%, and more preferably, between about 10 and about 60%, by volume of the feed gas mixture.

We have also discovered that the fluorinated hydrocarbon compounds within the scope of our invention have C—F bond dissociation energies (BDE) high enough such that C—F bond rupture does not occur at reaction temperatures typically used for olefin epoxidation. BDE values in excess of 110 kcal/mole, and more preferably, in excess of 120 kcal/mole are required to ensure thermal stability under reactions, such that formation of AgF does not occur.

In addition, the absence of reactive and acidic C—H bonds on the fluorinated hydrocarbon is required to ensure that abstraction of HF from the fluorinated hydrocarbon does not occur since reaction of HF with Ag forms Ag—F, which is inactive for olefin epoxidation. The location of the reactive C—H bond on fluorinated hydrocarbon is not material, although it is known from U.S. Pat. No. 4,950,773 that C—H bonds vicinal to, or adjacent, to C—X bonds, where X=Cl, Br, F, are more reactive than C—H bonds which are geminal to C—F bonds (H— and F— bonded to the same C atom). For totally perfluorinated hydrocarbons, there are no remaining C—H bonds. In these cases, the only factor to be considered is the BDE of the various C—F bonds. Typically, BDE values are primary C—F>secondary C—F>tertiary C—F bonds.

Examples of fluorinated hydrocarbons useful in the process of our invention include without limitation $CF_4$, $CHF_3$, and $C_2F_6$. Hexafluoroethane is especially preferred, since it contains only primary C—F bonds with a BDE of 126.8 kcal/mole and has a high molar heat capacity, favorable for heat management and flammability control in the epoxidation reactor.

Catalyst and Catalyst Preparation

The supported silver epoxidation catalysts that may be used in the process of our invention are known materials which may be prepared according to published procedures. Various alkali salt and thallium(I) salt promoters, various Ag salts used as Ag catalyst precursors, and various catalyst carriers used to support the promoted Ag catalysts have been discussed in earlier patents. Thermal and chemical methodologies used to generate active and selective promoted silver catalysts have also been described. See, for example, the following patents: J. L. Stavinoha et al., U.S. Pat. No. 5,362,890 (1994); J. R. Monnier et al., U.S. Pat. No. 5,138,077 (1992); J. R. Monnier et al., U.S. Pat. No. 4,950,773 (1990); J. E. Buffum et al., U.S. Pat. No. 5,145,824 (1992); M. M. Bhasin et al., U.S. Pat. No. 4,916,243 (1990); and A. M. Lauritzen, U.S. Pat. No. 4,833,261 (1989).

These references describe in great detail and in name different promoter salts and ranges of promoter salt loadings that have been used to promote both ethylene and butadiene and related olefins for selective epoxidation. Likewise, the above patents describe in great detail and in name specific Ag salts and ranges of silver salt precursors that have been used to generate promoted silver catalysts for both ethylene and butadiene and related olefins for selective epoxidation. Moreover, the above references specify in great detail and in name inert carriers that have been used to support the above catalyst components to carry out the epoxidation of ethylene, butadiene, and related olefins for selective epoxidation. Finally, the above patents discuss in great detail synthetic methodologies used to generate active and selective promoted, silver catalysts for ethylene, butadiene, and related olefin epoxidation. Familiarity with the content of those patents are presumed and are therefore not recited herein. The contents of which, however, are all hereby incorporated by reference.

The preferred epoxidation catalyst for use in the present invention is a Cs-promoted, supported Ag catalyst. Such a catalyst has been described in the literature and can be prepared using methods currently employed in the art.

Olefin Reactants and Reaction Conditions

The olefin reactants that may be used in the process of our invention include norbornene, norbornadiene and olefins having the general formula

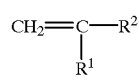

(I)

wherein $R^1$ is hydrogen or alkyl and $R^2$ is hydrogen, an aryl group, a tertiary alkyl group such as tertiary butyl, tertiary amyl, or tertiary octyl, or the group having the formula

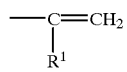

with the proviso that $R^1$ contains no hydrogen atoms in a position allylic to the ethylenic unsaturation, i.e., the >C=C< group or groups. The alkyl groups represented by $R^1$ may be unsubstituted or substituted alkyl having up to about 12 carbon atoms. Such alkyl groups preferably are unsubstituted alkyl of up to about 4 carbon atoms.

When the reactant is an olefin having the formula

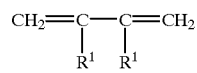

the $R^1$ substituents may be the same or different.

The aryl groups represented by $R^2$ may be unsubstituted or substituted carbocyclic aryl having 6 to 10 carbon atoms, e.g., unsubstituted and substituted phenyl and naphthyl radicals. Examples of the substituents which may be present on the aryl groups include alkyl of up to about 4 carbon atoms, alkoxy of up to about 4 carbon atoms, halogen such as chloro and bromo, hydroxy, vinyl, and the like so long as none of the substituents have a hydrogen allylic to a double bond.

The epoxides produced from the olefins of formula (I) in accordance with the epoxidation process described herein have the general formula

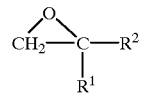

(II)

wherein $R^1$ and $R^2$ are defined above. The process provided by our invention is especially useful for the selective monoepoxidation of ethylene to ethylene oxide and 1,3-butadiene to 3,4-epoxy-1-butene.

Our novel process may be carried out at a temperature in the range of about 100° to 400° C., with the range of 150° to 300° C. being particularly preferred. The pressure within the epoxidation zone may range from about 0.5 to about 30 bars, preferably from about 1 to about 20 bars. It is apparent that the particular combination of temperature and pressure is selected so as to maintain all of the components of the feed to the epoxidation zone in the gaseous state.

As mentioned above, the advantages of the present invention may be achieved by feeding to the epoxidation zone a gas mixture comprising from about 5 to about 70% by volume, and more preferably, from about 10 to about 60% by volume of the fluorinated hydrocarbon. Normally, the feed gas mixture will also contain from about 5 to about 50% by volume of the olefin reactant, from about 3 to about 40% by volume of oxygen, and 0 to about 80% by volume of other components such as paraffin hydrocarbon containing 1 to 6 carbon atoms, organic halide, water, nitrogen, carbon dioxide, argon, helium, and recycled epoxide product.

To further illustrate the present invention and the advantages thereof, the following specific examples are provided. It is to be understood that these examples are merely intended to be illustrative and not limitative.

EXAMPLES

Catalyst Evaluations

For all catalyst evaluations, catalyst samples were ground and sieved to 18/25 mesh (between 0.71 and 1.00 mm in diameter) and loaded into reactors. Reactor dimensions were 0.375" OD stainless steel reactor with an inside diameter of 0.305". The reactor had an overall length of 23.7 inches and the catalyst was maintained inside the tubular reactor on a stainless steel mesh screen that supported the catalyst charge of approximately 12.0 grams in the middle of the reactor. A thermowell was inserted in the middle of the catalyst bed. The catalyst bed temperature was determined by moving a smaller ID thermocouple up and down inside the thermowell to determine the hot spot in the 12" long catalyst bed. The temperatures reported in the examples are the hot spot in the bed. Surrounding all but the ends of the tubular reactor was a 1.0" OD brass jacket into which the 0.375" tube had been press fitted. The 1" OD brass jacket helped to maintain isothermal conditions throughout the length of the catalyst bed by acting as an efficient heat sink. Pressure was maintained at the desired level by using either a needle valve to restrict flow or by a spring loaded, back pressure regulator. Below the pressure letdown, the gas flow was at approximately 14.7 psia. The gas flow was directed through an in-line gas-sampling network that permitted real time, accurate analysis of catalyst performance. Contents of a gas sample loop were analyzed using a Hewlett-Packard gas chromatograph employing a Poraplot Q column hooked to a thermal conductivity detector. This detector gave quantitative analyses for oxygen, carbon dioxide, water, butadiene, 3,4-epoxy-1-butene, and n-butane. Further, by means of a switching valve, a diverted slipstream of the feed gas above the catalyst could be analyzed to determine the feed gas composition; comparison with the analysis of the product stream permitted calculation of the conversion of butadiene feed and selectivity to epoxybutene. As used herein, conversion is the mole percent conversion of butadiene defined as:

$$\frac{\text{Moles butadiene converted to products}}{\text{Moles butadiene fed}} \times 100,$$

and selectivity is the percent selectivity to 3,4-epoxy-1-butene defined as:

$$\frac{\text{Moles butadiene converted to 3,4-epoxy-1-butene}}{\text{Moles butadiene converted to all products}} \times 100.$$

High Pressure Evaluation

For high-pressure operation, gas delivery was accomplished using mass flow controllers for oxygen, propane, ppm levels of 2-chlorobutane, and hexafluoroethane. Butadiene was added as a liquid by means of a dual syringe-pump assembly, which permitted continuous delivery of butadiene at high-pressure conditions. The liquid butadiene was flash vaporized into the gas feed line in a high temperature, liquid vaporizer maintained at 100° C. The blended gas phase composition was preheated and passed over the catalyst and performance subsequently determined.

Before exposure to reaction gas feeds, each catalyst was pretreated at 250° C. in a feedstream containing 20% oxygen in 80% helium for approximately 2 hrs, followed by exposure to a gas stream containing 10 ppm of 2-chlorobutane. The catalyst was then evaluated for epoxybutene formation.

Evaluation at Atmospheric Pressure

The same type of stainless steel reactors with brass jackets was used for the one-atmosphere evaluation experiments. In-line analyses were conducted using similar gas sampling methods and gas chromatographic analysis. Conversions of butadiene and selectivity to epoxybutene are defined as above. All feed compositions, with the exception of $CCl_4$, were added to the feedstream using mass flow controllers. Specifically, oxygen, butadiene, n-butane, ppm levels of 2-chlorobutane, trifluoromethane ($HCF_3$), hexafluoroethane ($C_2F_6$), 1,1,2,2-tetrafluoroethane (HFC-134a), octafluoropropane ($C_3F_8$), and n-decafluorobutane (n-$C_4F_{10}$) were added to the feedstream using mass flow controllers. Carbon tetrachloride ($CCl_4$) was supplied to the feedstream from a vapor liquid equilibrium saturator, whereby an inert sweep gas, typically helium, was passed through liquid $CCl_4$, maintained at a predetermined temperature. By proper combination of saturator temperature and sweep gas flow, the desired concentration of $CCl_4$ was added to the feedstream contacting the catalyst.

Before evaluation, all catalysts were pretreated by calcining in a flowing stream of 20% oxygen and 80% helium for 2 hours at 250° C., followed by pretreatment in 20% hydrogen and 80% helium for one hour at 200° C. Catalysts were then ready to be evaluated for activity and selectivity to epoxybutene.

Comparative Example 1

3.0 grams of a catalyst containing 700 ppm of Cs as a promoter and 15% Ag supported on a fused alpha alumina carrier were pretreated and evaluated at one atmosphere pressure as described above. The catalyst was first exposed at 190° C. and 200° C. for a total of 23 hrs to a feed gas made up of 67% n-$C_4H_{10}$, 16.5% $C_4H_6$, 16.5% $O_2$, and 2 ppm 2-chlorobutane. After 23.0 hrs, the feed gas was switched to 33% n-$C_4H_{10}$, 14% He, 20% $CCl_4$, 16.5% $C_4H_6$, 16.5% $O_2$, and 2 ppm 2-chlorobutane. Catalyst performance at 190° C. was measured 3 min and 20 min after $CCl_4$ addition and at 195° C. after exposure to $CCl_4$ for a total of 35 min. The results are summarized in Table 1.

TABLE 1

Effect of $CCl_4$ on Performance

| Temp. (°C.) | Run Time (hrs) | $CCl_4$ in Feed (vol %) | $C_4H_6$ Conversion (%) | EpB Selectivity (%) |
|---|---|---|---|---|
| 190 | 20.50 | 0 | 5.33 | 91.10 |
| 195 | 20.80 | 0 | 6.69 | 90.85 |
| 190 | 23.00 | 0 | 5.23 | 91.01 |
| 20% $CCl_4$ added to feed after 23.30 hrs on-line. | | | | |
| 190 | 23.35 | 20 | 0.64 | 12.47 |
| 190 | 23.63 | 20 | 0.05 | 0.00 |
| 195 | 23.88 | 20 | 0.01 | 0.00 |

The results show that exposure to 20% $CCl_4$ for periods as short as 0.05 hrs results in massive loss of activity. After only 0.58 hrs of total exposure to 20% $CCl_4$, total loss of activity occurs. Analysis of the catalyst after reaction by x-ray diffraction indicated that the catalytically active Ag surface had been completely and irreversibly converted to AgCl, which is inactive for olefin epoxidation. The bond dissociation energy (BDE) for the C—Cl bond in $CCl_4$ has been reported to be 73.1 kcal/mole ("Handbook of Chemistry and Physics, $73^{rd}$ Edition," D. R. Lide, editor-in-chief, CRC Press, Boca Raton, Fla., 1992, pp. 9–138 to 9–141).

Comparative Examples 2–4

Catalyst samples containing 700 ppm Cs, 15% Ag supported on fused alpha alumina were ground and sieved to 18/15 mesh. Approximately 12.0 gms of sieved catalyst were used for each experiment. Fresh catalyst charges were used for each experiment. Each catalyst was pretreated as referenced in Comparative Example 1 before evaluation. The catalysts were allowed to reach steady-state activity at 200° C. in a feed composition of 67% n-$C_4H_{10}$, 16.5% $C_4H_6$, 16.5% $O_2$, and 2 ppm 2-chlorobutane before the addition of 20% fluorinated hydrocarbon to the feedstream. Catalysts were typically evaluated for a period of 20–24 hrs in the above feedstream before steady-state performance conditions were attained. After steady-state reaction rates were attained, the feed composition was changed to 47% n-$C_4H_{10}$, 20% fluorinated hydrocarbon, 16.5% $C_4H_6$, 16.5% $O_2$, and 2 ppm 2-chlorobutane. In all cases, total flow rate was maintained at 300 ml (STP)/min. Catalytic activity ($C_4H_6$ conversion) and selectivity to epoxybutene (EpB) were followed as a function of exposure time to the feed containing 20% fluorinated hydrocarbon. The results are summarized below in Table 2 for catalyst performance using 20% $C_3F_8$ (Comparative Example 2), 20% n-$C_4F_{10}$ (Comparative Example 3), and 20% HFC-134a (Comparative Example 4) in the feed gas to the catalyst. Catalyst performance before addition of the fluorinated hydrocarbon is noted as 0 hrs of addition.

TABLE 2

Effect of Certain Fluorinated Hydrocarbons on Catalyst Performance

| Comparative Example No. | Fluorinated Hydrocarbon | Length of Time Added (hrs) | Conversion of $C_4H_6$ (%) | Selectivity to EpB (%) | C-F BDE (kcal/mole) |
|---|---|---|---|---|---|
| 2 | $C_3F_8$ | 0 | 26.7 | 86.2 | 110 |
|   |   | 2 | 12.8 | 92.2 | (secondary C-F) |
|   |   | 3 | 9.5 | 92.1 | 123 |
|   |   | 7 | 2.7 | 92.6 | (primary C-F) |
|   |   | 17 | 0.9 | 75.3 |   |
| 3 | n-$C_4F_{10}$ | 0 | 22.5 | 88.1 | 110 |
|   |   | 2 | 0 | 0 | (secondary C-F) |
|   |   | 4 | 0 | 0 | 123 |
|   |   | 8 | 0 | 0 | (primary C-F) |
| 4 | HFC-134a | 0 | 27.2 | 85.5 | C-F bond: |
|   |   | 3 | 25.7 | 86.3 | 120 |
|   |   | 23 | 19.2 | 91 | C-H bond: |
|   |   | 37 | 7.7 | 93.1 | 95 |
|   |   | 55 | 3.5 | 90.9 |   |

The rapid and irreversible loss of catalytic activity is due to the reactivity of abstracted F atoms with the Ag surface of the Cs-promoted, Ag/$Al_2O_3$ catalyst. In the case of HFC-134a, the BDE of the C—H bond contributes to facile formation of H—F. The formation of AgF renders the Ag catalyst inactive for butadiene epoxidation.

Example 1

12.1 grams of a catalyst containing 700 ppm of Cs as a promoter and 15% Ag supported on a fused alpha alumina carrier were pretreated and evaluated at one atmosphere pressure as described above. The catalyst was first exposed at 200° C. for a total of 19 hrs to a feed gas made up of 67% n-$C_4H_{10}$, 16.5% $C_4H_6$, 16.5% $O_2$ and 2 ppm 2-chlorobutane. After 19 hrs, the feed composition was changed to 47% n-$C_4H_{10}$, 20% $C_2F_6$, 16.5% $C_4H_6$, 16.5% $O_2$, and 2 ppm 2-chlorobutane. For both feed compositions, total flow rate was maintained at 300 ml (STP)/min. Catalytic activity ($C_4H_6$ conversion) and selectivity to epoxybutene (EpB) were followed as a function of exposure time to the feed containing 20% $C_2F_6$. Catalyst performance is summarized in Table 3 below.

TABLE 3

Effect of 20% $C_2F_6$ on Catalyst Performance

| Length of Time $C_2F_6$ Added (hrs) | Conversion of $C_4H_6$ (%) | Selectivity to EpB (%) |
|---|---|---|
| 0 | 22.2 | 89.3 |
| 2 | 22.5 | 88.7 |
| 5 | 22.4 | 89.3 |
| 9 | 22.4 | 89.1 |
| 21 | 21.6 | 88.9 |
| 35 | 20.8 | 88.9 |
| 49 | 20.5 | 89.5 |
| 69 | 20.3 | 89.5 |
| 105 | 20.5 | 89.2 |
| 139 | 20.3 | 89.3 |

The bond dissociation energy (BDE) of the C—F bonds in $C_2F_6$ is 127 kcal/mole (Bryant, W. M. D., *J. Polymer Science*, vol. 56, pages 277–296, 1962). This bond energy is considerably higher than bond dissociation energies of C—F bonds in Comparative Examples 2–4 and is much larger than the C—Cl bond dissocaiation energy in Comparative Example 1. The resistance of $C_2F_6$ to F abstraction by the promoted Ag catalyst to form AgF results in stability of the Cs-promoted, Ag catalyst, even at concentrations as high as 20% in the feedstream and at temperatures as high as 200° C. The bond dissociation energy of the C—F bond in HFC-134a is comparable to that for $C_2F_6$. However, the presence of acidic C—H bonds in HFC-134a favor F abstraction by dehydrofluorination to form HF, which results in catalyst deactivation the same way that F abstraction from $C_3F_8$ and n-$C_4F_{10}$ results in catalyst deactivation. Catalyst modification by dehydrohalogenation is disclosed in U.S. Pat. No. 4,950,773 (August 1990).

Example 2

12.0 grams of a catalyst containing 700 ppm of Cs as a promoter and 15% Ag supported on a fused alpha alumina carrier were pretreated and evaluated at one atmosphere pressure as described above. The catalyst was first exposed at 200° C. for a total of 48 hrs to a feed gas made up of 67% n-$C_4H_{10}$, 16.5% $C_4H_6$, 16.5% $O_2$, and 2 ppm 2-chlorobutane. After 48 hrs, the feed composition was changed to 47% n-$C_4H_{10}$, 20% $HCF_3$, 16.5% $C_4H_6$, 16.5% $O_2$, and 2 ppm 2-chlorobutane. For both feed compositions, total flow rate was maintained at 300 ml (STP)/min. Catalytic activity ($C_4H_6$ conversion) and selectivity to epoxybutene (EpB) were followed as a function of exposure time to the feed containing 20% $HCF_3$. Catalyst performance is summarized in Table 4 below.

TABLE 4

Effect of 20% $HCF_3$ on Catalyst Performance

| Length of Time $HCF_3$ Added (hrs) | Conversion of $C_4H_6$ (%) | Selectivity to EpB (%) |
|---|---|---|
| 0 | 12.2 | 92.0 |
| 2 | 12.8 | 92.2 |
| 10 | 13.0 | 92.7 |
| 20 | 13.0 | 93.3 |
| 30 | 13.5 | 93.5 |
| 50 | 13.8 | 93.5 |
| 70 | 13.2 | 93.8 |

The bond dissociation energy of the C—F bond in $HCF_3$ is 128 kcal/mole ("Handbook of Chemistry and Physics, 73$^{rd}$ Edition," D. R. Lide, editor-in-chief, CRC Press, Boca Raton, Fla., 1992, pp. 9–138 to 9–141). This high bond dissociation energy results in excellent stability of $HCF_3$ in the presence of the Cs-promoted, Ag catalyst. Thus, no deactivation occurs, even in the presence of 20% $HCF_3$ in the feedstream. While $HCF_3$ does contain a C—H bond, both H and F are attached to the same C atom. This results in much greater stability and resistance to dehydrofluorination to form HF, which is markedly different from the case of HFC-134a, where the reactive H and F are on adjacent C atoms.

Example 3

12.0 grams of a Cs-promoted, Ag catalyst promoted on fused alpha alumina containing 1310 ppm Cs and 15.8% Ag were evaluated at high-pressure conditions using a reactor and analytical system as described above. The catalyst was pretreated at 250° C. for 2 hrs in 20% $O_2$, balance inert gas and an additional 30 minutes in a gas stream containing 10 ppm 2-chlorobutane at 180° C. The catalyst was then exposed to a gas stream containing 9% $C_4H_6$, 17% $O_2$, balance $C_3H_8$+2 ppm of 2-chlorobutane at 200° C. and 15 psia total pressure. After 50 hours, the overall pressure was increased to 45 psia total pressure and the temperature raised to 205° C. The total gas flow rate was maintained constant at 450 ml (STP)/min.

After approximately 150 hours on-line, the reactor pressure was increased to 60 psia. Temperature and total flow were held constant at 205° C. and 450 ml (STP)/min, respectively. Gas feed compositions were changed as summarized in Table 5 to, at times, include $C_2F_6$ as a feed component; when $C_2F_6$ was added, the $C_4H_6$ and $O_2$ concentrations were also increased. The overall gas compositions were selected to ensure that operation remained in the non-flammable region, based on temperature and pressure. Of course, addition of $C_2F_6$ permitted safe, non-flammable gas compositions with higher $C_4H_6$ and $O_2$ concentrations, illustrating an especially important benefit of using $C_2F_6$ as the preferred inert diluent.

TABLE 5

Effect of 20% $C_2F_6$ on Catalyst Performance at 60 psia Pressure

| Feed Concentration (%) at 60 psia Pressure | | | | Butadiene Conversion | EpB Selectivity |
|---|---|---|---|---|---|
| $C_4H_6$ | $O_2$ | $C_3H_8$ | $C_2F_6$ | (%) | (%) |
| 9 | 22 | 69 | 0 | 13.7 | 85.6 |
| 9 | 26 | 45 | 20 | 16.5 | 86.9 |
| 15 | 21 | 64 | 0 | 15.6 | 86.7 |
| 15 | 25 | 40 | 20 | 17.4 | 87.6 |

The above data illustrate very clearly the benefits of replacing some of the propane diluent with $C_2F_6$. Replacement of 20% $C_3H_8$ with $C_2F_6$ permits non-flammable and non-explosive operation with higher concentrations of $O_2$ at two different levels of $C_4H_6$ concentration. At 9% $C_4H_6$ concentration, the presence of $C_2F_6$ allows $O_2$ to be increased from 22 to 26%; while at 15% $C_4H_6$, $O_2$ levels can be raised from 21 to 25%. In both cases, conversion and selectivity increased, resulting in higher yields of epoxybutene.

Example 4

12.0 grams of a catalyst containing 700 ppm of Cs as a promoter and 15% Ag supported on a fused alpha alumina carrier were pretreated and evaluated at one atmosphere pressure as described above. The catalyst was first exposed at 190° C. for a total of 140 hrs to a feed gas made up of 70% n-$C_4H_{10}$, 12% $C_4H_6$, 18% $O_2$, and 2 ppm 2-chlorobutane. After 140 hrs, the feed composition was changed to 50% $C_2F_6$, 20% $C_4H_6$, 30% $O_2$, and 2 ppm 2-chlorobutane for a period of 24 hrs. For both feed compositions, total flow rate was maintained at 155 ml (STP)/min. The feed composition of 70% n-$C_4H_{10}$, 12% $C_4H_6$, 18% $O_2$, and 2 ppm 2-chlorobutane was selected to give the most reactive, yet non-flammable and non-explosive, feed composition attainable at the described reaction conditions. This feed composition maximizes the activity for EpB formation. The feed composition containing 50% $C_2F_6$ is non-flammable and non-explosive at any reaction or process condition. Any combination of $C_4H_6$ and $O_2$ totalling 50% of the total gas feed could be safely used both in the reactor and downstream processing below the reactor. This composition was used for 24 hours with no decrease in catalyst performance. The reaction temperature was then raised to 200° C. and the catalyst exposed again to a feed containing 70% n-$C_4H_{10}$, 12% $C_4H_6$, 18% $O_2$, and 2 ppm 2-chlorobutane and then to 50% $C_2F_6$, 20% $C_4H_6$, 30% $O_2$, and 2 ppm 2-chlorobutane. The results are summarized below in Table 6. Percent EpB produced refers to concentration of EpB in the product stream, expressed in volume percent of the total gas stream. It is necessary to express catalyst activity in this manner, since the $C_4H_6$ composition varies from 12% to 20% in the examples in Table 6.

TABLE 6

Effect of 50% $C_2F_6$ on Catalyst Performance

| Reaction Temperature (° C.) | Feed Composition (%) | | | | EpB Produced (%) | Selectivity to EpB (%) |
|---|---|---|---|---|---|---|
| | n-$C_4H_{10}$ | $C_2F_6$ | $C_4H_6$ | $O_2$ | | |
| 190 | 70 | 0 | 12 | 18 | 0.80 | 92.8 |
| 190 | 0 | 50 | 20 | 30 | 1.44 | 91.2 |
| 200 | 70 | 0 | 12 | 18 | 1.47 | 91.7 |
| 200 | 0 | 50 | 20 | 30 | 1.79 | 92.2 |

The data in Table 6 indicate that enhanced, stable catalyst performance occurs when feed levels contain as high as 50% $C_2F_6$. Further, the presence of 50% $C_2F_6$ in the feedstream renders the entire butadiene epoxidation process non-flammable and non-explosive. Operation of olefin epoxidation processes in safe non-flammable and non-explosive operational regimes is a very important consideration in operation of commercial, large-scale olefin epoxidation processes. Secondly, the data in Table 6 show that catalyst deactivation does not occur for feedstreams containing stable fluorohydrocarbons at the very high levels necessary to ensure non-flammable and non-explosive operation. The safe operability regime permits any desirable combination of olefin and $O_2$ totaling 50% of the total feed composition. Of course, it is understood that organic chloride levels, in this case, 2-chlorobutane, be continually added to the feedstream in ppm levels.

Comparative Example 5 and Example 5

Computer simulations of a commercial reactor tube were conducted using kinetic parameters fitted for the epoxidation of ethylene to ethylene oxide with a commercial silver catalyst. A two-dimensional heat and mass transfer model of the epoxidation reaction (taking into account transport in both axial and radial dimensions) was found to be in excellent agreement with the experimentally measured conversions, selectivities, and temperature profiles. The computer simulation was used to determine the expected selectivity, conversion, and temperature profile for the conversion of ethylene to ethylene oxide with either methane or perfluoroethane as the diluent or ballast gas. Each simulation run was conducted at 2 percentage points below the maximum safe oxygen concentration for the given system at a nominal maximum temperature of 250° C., outlet pressure of 1.17 MPa, constant reactor volume of 20.8 cubic meters, and constant centerline temperature at the hot spot. A summary of feed concentrations and simulation results is given in Table 7 below for a production rate of 100 million pounds per year of ethylene oxide. The maximum safe oxygen concentation is increased by 5 percentage points by the replacement of methane with $C_2F_6$.

TABLE 7

Effect of Diluent on Reactor Performance

| | Comparative Example 5 | Example 5 |
|---|---|---|
| Inlet Conditions | | |
| Reactor Length (m) | 10.7 | 7.6 |
| Inside Tube Diameter (m) | 0.041 | 0.041 |
| Number of Tubes | 1486 | 2080 |
| Reactor Volume (m$^3$) | 20.8 | 20.8 |
| Ethylene Feed Concentration | 35 mole % | 35 mole % |
| Diluent Concentration | 38.0 mole % CH$_4$ | 33.6 mole % C$_2$F$_6$ |
| Maximum Safe Oxygen Level | 11.0 mole % | 16.0 mole % |
| Oxygen Level Used in Simulation | 9.0 mole % | 14.0 mole % |
| Outlet Conditions | | |
| Outlet Pressure (MPa) | 1.17 | 1.17 |
| Centerline Temperature at Hot Spot (°C.) | 255 | 255 |
| Average Radial Temperature at Hot Spot (°C.) | 251 | 253 |
| Radial Temperature Differential at Hot Spot (°C.) | 8.5 | 4.6 |
| Ethylene Conversion (%) | 10.4 | 11.9 |
| Selectivity to Ethylene Oxide (%) | 75.5 | 77.4 |
| Space-Time Yield (lb EO/lb catalyst-hr) | 11.0 | 18.2 |
| Outlet Ethylene Oxide Concentration | 2.77 mole % | 3.26 mole % |

The simulations clearly show the advantage of replacing the methane diluent with $C_2F_6$. The reactor is made more isothermal (radial and axial temperature gradients decreased), a higher EO concentration is seen at the reactor outlet with a shorter bed, and the space-time yield is increased with $C_2F_6$. At equivalent reactor volumes, the production rate and space time yield are increased by 64% by replacing methane with $C_2F_6$.

As seen from the above, addition or replacement of diluent hydrocarbons in epoxidation feed gases with certain fluorinated hydrocarbon compounds in accordance with our invention provides a number of advantages. Those advantages include:

1. Increasing the maximum safe oxygen concentration. This allows the use of higher $O_2$ levels than possible with hydrocarbon diluents, while maintaining operation outside of the flammability envelope. An increase in $O_2$ partial pressure increases the rate of epoxidation reactions—resulting in a higher space-time-yield.
2. Rendering the reactor more isothermal. The fluorinated hydrocarbon compounds suitable for use in the present invention have high heat capacities, much higher than methane, nitrogen, and other common diluents. Since epoxidations are highly exothermic and prone to thermal runaways, the addition of those fluorinated hydrocarbons increases the heat capacity of the gas in the reactor, making the reactor more isothermal. A more isothermal reactor is easier to control and safer to operate.
3. Improving safety. Flammable hydrocarbons are replaced by non-flammable fluorinated hydrocarbon compounds. The inventory of flammable gas in the reactor and recycle loop is thus reduced. Less flammable gas would be released in an accident, and the operation of the plant is made safer by this change.

While the invention has been described with reference to working examples and preferred embodiments, it is to be understood that variations and modifications may be resorted to as will be apparent to those skilled in the art. Such variations and modifications are to be considered within the purview and scope of the invention as defined by the claims appended hereto.

We claim:

1. A process for the selective epoxidation of non-allylic olefins, said process comprising the step of:
    contacting a gas mixture comprising a non-allylic olefin, oxygen, and a fluorinated hydrocarbon with a silver epoxidation catalyst at conditions effective to epoxidize the non-allylic olefin,
    wherein said fluorinated hydrocarbon has a C—F bond dissociation energy of 110 kcal/mole or greater, and sufficiently non-acidic C—H bonds, if present, so as to avoid abstraction of HF from the fluorinated hydrocarbon under reaction conditions.
2. The process according to claim 1, wherein said non-allylic olefin is ethylene or 1,3-butadiene.
3. The process according to claim 1, wherein said fluorinated hydrocarbon has a C—F bond dissociation energy of 120 kcal/mole or greater.
4. The process according to claim 1, wherein said fluorinated hydrocarbon is $CF_4$, $C_2F_6$, $CHF_3$, or mixtures thereof.
5. The process according to claim 1, wherein said gas mixture comprises from about 5 to about 70 vol % of said fluorinated hydrocarbon.
6. The process according to claim 5, wherein said gas mixture comprises from about 10 to about 60 vol % of said fluorinated hydrocarbon.
7. A process for the selective epoxidation of ethylene, said process comprising the step of:
    contacting a gas mixture comprising ethylene, oxygen, and from about 5 to about 70 vol % of a fluorinated hydrocarbon with a silver epoxidation catalyst at conditions effective to epoxidize the non-allylic olefin,
    wherein said fluorinated hydrocarbon has a C—F bond dissociation energy of 120 kcal/mole or greater, and sufficiently non-acidic C—H bonds, if present, so as to avoid abstraction of HF from the fluorinated hydrocarbon under reaction conditions.
8. The process according to claim 7, wherein said fluorinated hydrocarbon is $CF_4$, $C_2F_6$, $CHF_3$, or mixtures thereof.
9. The process according to claim 7, wherein said gas mixture comprises from about 10 to about 60 vol % of said fluorinated hydrocarbon.
10. A process for the selective epoxidation of 1,3-butadiene, said process comprising the step of:
    contacting a gas mixture comprising 1,3-butadiene, oxygen, and from about 5 to about 70 vol % of a fluorinated hydrocarbon with a silver epoxidation catalyst at conditions effective to epoxidize the non-allylic olefin, wherein said fluorinated hydrocarbon has a C—F bond dissociation energy of 120 kcal/mole or greater, and sufficiently non-acidic C—H bonds, if present, so as to avoid abstraction of HF from the fluorinated hydrocarbon under reaction conditions.

11. The process according to claim 10, wherein said fluorinated hydrocarbon is $CF_4$, $C_2F_6$, $CHF_3$, or mixtures thereof.

12. The process according to claim 10, wherein said gas mixture comprises from about 10 to about 60 vol % of said fluorinated hydrocarbon.

* * * * *